United States Patent
Cataldo et al.

(10) Patent No.: US 9,134,280 B2
(45) Date of Patent: Sep. 15, 2015

(54) METHOD FOR TESTING PIPELINE WELDS USING ULTRASONIC PHASED ARRAYS

(75) Inventors: Giuseppina Cataldo, Milan (IT); Olivier Diligent, Elancourt (FR)

(73) Assignee: SAIPEM S.P.A., San Donato Milanese (IT)

( * ) Notice: Subject to any disclaimer, the term of this patent is extended or adjusted under 35 U.S.C. 154(b) by 439 days.

(21) Appl. No.: 13/201,956

(22) PCT Filed: Feb. 1, 2010

(86) PCT No.: PCT/EP2010/051172
§ 371 (c)(1),
(2), (4) Date: Aug. 17, 2011

(87) PCT Pub. No.: WO2010/097269
PCT Pub. Date: Sep. 2, 2010

(65) Prior Publication Data
US 2011/0296923 A1    Dec. 8, 2011

(30) Foreign Application Priority Data
Feb. 25, 2009 (GB) .................................. 0903232.7

(51) Int. Cl.
*G01N 29/04* (2006.01)
*G01N 29/26* (2006.01)
*G01N 29/44* (2006.01)

(52) U.S. Cl.
CPC ............ *G01N 29/262* (2013.01); *G01N 29/043* (2013.01); *G01N 29/4445* (2013.01); *G01N 2291/106* (2013.01); *G01N 2291/2634* (2013.01); *G01N 2291/2675* (2013.01)

(58) Field of Classification Search
CPC ...................... G01N 29/043; G01N 2291/2675
USPC .......................................................... 73/632
See application file for complete search history.

(56) References Cited

U.S. PATENT DOCUMENTS

| 4,570,487 A | 2/1986 | Gruber |
| 6,405,596 B1 | 6/2002 | Kruzic |

(Continued)

FOREIGN PATENT DOCUMENTS

| WO | WO 01/71338 A1 | 9/2001 |
| WO | WO 02/31487 A2 | 4/2002 |
| WO | WO 2005/045418 A1 | 5/2005 |

OTHER PUBLICATIONS

International Search Report (PCT/ISA/210) for PCT/EP2010/051172 dated May 25, 2010.

(Continued)

*Primary Examiner* — John Chapman, Jr.
(74) *Attorney, Agent, or Firm* — Buchanan Ingersoll & Rooney PC

(57) ABSTRACT

NDT inspection of an austenitic weld between two CRA Clad pipes using a phased ultrasonic transducer array system is described. The method may be performed during laying of gas/oil fatigue sensitive pipelines, for example, at sea. Two types of UT inspection may be generated simultaneously by a Phased Array on each side (Upstream and Downstream) of a girth weld. Firstly, mode converted longitudinal waves are used. These waves have properties that they propagate well. Shear waves are also used. The combination of these two ultrasonic waves, with the addition of surface waves, enables 100% of the girth weld to be inspected to the standard required in fatigue sensitive welds, such as Steel Catenary Risers. Shear waves and compression waves are emitted substantially contemporaneously. Defects may be detected and measured using time of flight information and amplitudes of radiation detected on reflection and on diffraction from the defect.

20 Claims, 8 Drawing Sheets

(56) References Cited

U.S. PATENT DOCUMENTS

| | | |
|---|---|---|
| 6,497,150 B1 | 12/2002 | Kruzic |
| 6,813,950 B2 | 11/2004 | Glascock et al. |
| 2007/0000328 A1 | 1/2007 | Buttram |
| 2007/0261495 A1 | 11/2007 | Van Der Ent et al. |
| 2008/0127732 A1* | 6/2008 | Owens et al. ............... 73/632 |
| 2009/0095087 A1* | 4/2009 | Yamano ................. 73/622 |

OTHER PUBLICATIONS

Written Opinion (PCT/ISA/237) for PCT/EP2010/051172 dated May 25, 2010.

United Kingdom Search Report for GB 0903232.7 dated May 27, 2009.

M. Miles et al., "Pipeline Girth Weld Inspections using Ultrasonic Phased Arrays", American Society of Mechanical Engineers, Pressure Vessels and Piping Division (Publication) PVP, Jun. 2003, pp. 19-27, vol. 456.

J. De Raad et al., "Mechanized Ultrasonic Testing on Girth Welds During Pipeline Construction", Materials Evaluation, Aug. 1, 1997, pp. 890-895, vol. 55, No. 8.

M. Moles, "Phased Array Ultrasonic Inspection of Pipe Welds", Technical Paper—Society of Manufacturing Engineers—Welding Insights Conference 2007, Jun. 2007, 15 pages.

S. Chen et al., "The Design of an Ultrasonic Phased Array System on Pipelines' Weld Inspection", Proceedings of the Biennial International Pipeline Conference, Oct. 2004, pp. 905-908, vol. 2.

M. Moles, "Ultrasonic Phased Array", 7 pages, retrieved from the internet: http://www.olympusndt.com/en/lang/ultrasonic-phased-array/.

J.C. Drury, "Ultrasonic Flaw Detection for Technicians", Third Edition, Jun. 2004, 43 pages.

A. Erhard et al., "Ultrasonic Phased Array Technique for Austenitic Weld Inspection", 4 pages, retrieved from the internet: http://www.ndt.net/article/wcndt00/papers/idn192/idn192.htm.

"Phased Array Technical Guidelines, Useful Formulas, Graphs, and Examples", R/D Tech, 10 pages.

"Basic Concepts of Phased Array Ultrasonic Technology", R/D Tech, 13 pages.

"Main Concepts of Phased Array Ultrasonic Technology", R/D Tech, 23 pages.

W. Mayinger et al., "Dissimilar Metal Welds (DMW) in German LWR's", SMIRT Conference, 2001, pp. 1-23.

J. Van Der Ent et al., "Automatic Ultrasonic Inspection of Pipeline Girth Welds with a Corrosive Resistant Alloy (CRA) Layer", Asia-Pacific Conference on NDT, Nov. 2006, 16 pages.

"Standard Practice for Mechanized Ultrasonic Testing of Girth Welds Using Zonal Discrimination with Focused Search Units", ASTM International, Designation: E 1961-06, pp. 1-12.

"Introduction to Phased Array Ultrasonic Technology Applications", Advanced Practical NDT Series, Chapter 2, pp. 28-29, and 80-87.

E. Ginzel, "New ASTM Standard for Pipeline Inspection", NDT.net, Apr. 1999, 5 pages, vol. 4, No. 4.

E. Ginzel et al., "Application of Mechanized Ultrasonic Inspection to Manually Welded Pipeline Girth Welds", NDTnet, May 1997, 7 pages, vol. 2, No. 5.

* cited by examiner

METHOD FOR TESTING PIPELINE WELDS USING ULTRASONIC PHASED ARRAYS

BACKGROUND OF THE INVENTION

The present invention concerns a method for inspecting welds between pipe sections when laying pipelines. More specifically, but not exclusively, this invention relates to a method for the non-destructive inspection of welds between pipe sections using a phased ultrasonic transducer array system.

The present invention is particularly, but not exclusively, concerned with a non-destructive weld testing method used when laying oil or gas pipelines underwater. When laying a pipeline at sea it is customary to weld, on a lay-barge, individual pipe sections to a pipe string (the pipe string leading towards the seabed). The welding process takes place on the lay-barge. The pipe-string, when being laid, is under great tension and weld joints must be sufficiently strong to withstand the high forces imposed on them. As such, each time a pipe is welded to another pipe, extensive tests are made to ensure that the quality of the weld joint formed is sufficient.

It is customary to use non-destructive testing (NDT) techniques to inspect the quality of welds between pipe sections. International standards for NDT methods used in laying pipelines place strict limits on the accuracy of these methods. In order to assess whether a given weld is of sufficient quality, it is important that the NOT method used can reliably detect and provide accurate information about the size and location of any defects found in the weld. The time pressure that is present when laying pipelines at sea also means that it is important that any defects in the welds be detected and analysed very quickly.

Ultrasonic testing is a popular NDT technique for inspecting welds. Typically, ultrasonic sound waves are used to detect defects in the region of the weld. For most applications, shear waves (also called transverse waves) are used to detect and gauge the size of defects. Compression waves (longitudinal waves) are generally less suitable because the smallest size of defect detectable by means of compression waves is typically twice as large as the smallest size of defect detectable by means of shear waves in an otherwise identical set-up. Certain pipeline applications, however, use pipes internally clad with corrosion resistant alloy (CRA) materials such as austenitic stainless steel. The weld material in weld joints in such pipelines is also typically of austenitic material. Such austenitic materials have a coarse granular structure that skews and attenuates ultrasonic waves. Longitudinal waves are affected less than shear waves and are thus preferred for inspection. Welds in which the material welded together and/or the material in the heat-affected zone and/or the weld material (the filler material) itself comprises austenitic material will hereby be referred to as austenitic welds. Such ultrasonic testing is generally supplemented with other non-destructive tests to ensure reliability.

WO2005/045418 discloses a method for the ultrasonic inspection of an austenitic weld between two pipes. It uses two sets of ultrasound transducers placed either side of the weld. Accurate location and sizing of defects in spite of the skewing and attenuating properties of the weld material is achieved by using three different ultrasound beams. Firstly, two differently angled longitudinal beams are directed towards a given region. The detection and analysis of the ultrasound waves that result allow for detection of a defect. The size of the defect may then, optionally, be gauged by means of a third, shear-wave, beam of ultrasound radiation. In order to inspect different regions of the weld, the transducers need to be moved or different additional transducers used. It would appear that if the same transducers are used to inspect different locations then the transducers need to be moved manually. To perform NOT on a pipe weld with the apparatus of WO2005/045418, it would seem necessary either to realign the transducers for different locations and/or provide a large number of transducers.

The present invention seeks to mitigate one or more of the above-mentioned problems. Alternatively or additionally, the present invention seeks to provide an improved method for non-destructively testing a weld between two sections of metal pipe during the laying of a pipeline.

SUMMARY OF THE INVENTION

According to the invention, there is provided a method for the non-destructive inspection of a weld between a first metal pipe and a second metal pipe, wherein the method comprises the following steps:

forming a weld, preferably an austenitic weld, between two pipe-sections during a method of laying a pipeline, providing a plurality of ultrasonic transducers, able to transmit and detect ultrasonic radiation, comprising two or more ultrasonic transducers arranged as a phased array, emitting a first beam of ultrasonic radiation so as to be incident on a first region of the weld, emitting a second beam of ultrasonic radiation so as to be incident on a second region of the weld, and emitting a third beam of ultrasonic radiation so as to be incident on a third region of the weld, at least two of the first, second and third beams being emitted substantially contemporaneously, detecting radiation from the first, second and third regions resulting from the incidence of the first, second and third beams, extracting information from the detected radiation, and using such information to provide an indication from which the likelihood of a defect in the weld may be discerned.

The method may include a step of extracting amplitude information from the radiation detected. Amplitude information may provide information concerning the size of a defect. The step of extracting amplitude information may include detecting the amplitude of waves reflected from a defect. Amplitude information can be used to provide accurate indications of the size of a defect, as explained in further detail below. The method may include a step of extracting time of flight information, for example, time of flight of waves reflected by a defect.

A Time of Flight Diffraction (TOFD) technique may additionally be conducted. A TOFD technique may be used to carry out detection and characterisation of defects on or near the inner diameter surface of the pipes. For example, TOFD technique may be used to detect and characterise defects in the root zone or in the vicinity of the root zone. TOFD techniques may also be used to carry out detection and characterisation of defects in other regions.

The method may include extracting time of flight information and amplitude information from the detected radiation on a zone-by-zone basis. Combining all of these factors (extracting time of flight information, extracting amplitude information, and performing the inspection on a zone-by-zone basis) allows for correlation of data and provides a means of obtaining accurate detection and classification, for example by size and/or orientation, of defects in the region of the weld.

Preferably, the first beam is a focussed beam. Preferably, the first beam is emitted from the phased array. The first beam may be used in a "focussed mode" to inspect for defects on the bevel face as well as the surrounding material. The first beam is preferably incident on the weld as a longitudinal (compression) wave.

Longitudinal waves may be used to search for defects on the bevel face (the notional boundary between the pipe and the weld material) as well as the surrounding material (both in the weld and in the heat affected zone surrounding the weld). Longitudinal waves have the advantage that they propagate better in austenitic material than transverse (shear) waves, which makes the longitudinal waves better for detection and sizing of very small indications in austenitic material.

The second beam may be a wide beam. The second beam may be a divergent beam. The second beam may be used in a "wide beam mode" to perform volumetric inspections. Such volumetric inspections may look for defects and/or measure the porosity of the material in or around the weld region.

The second beam may be emitted from an ultrasonic transducer that does not form part of the phased array. The second beam may be a surface wave. The second beam may be used to perform surface inspections for defects at or near the outer diameter surface of the pipes.

The second beam may be emitted so as to be incident on the second region as a longitudinal wave. The second region may overlap with or be the same as the first region. The second region may be different from the first region.

Preferably, the third beam is a focussed beam. Preferably, the third beam is emitted from the phased array. Preferably, the third beam is emitted so as to be incident on the third region as a transverse wave. The third beam may be used in a "corroborative mode" as a conventional focussed transverse (shear) wave beam to also detect defects on the bevel face (effectively acting as a back-up/confirmation scan).

A focussed transverse wave (which may, but need not, be the third beam) may be used to detect defects on the bevel face. A focussed transverse wave may be used to detect defects on or near the inner diameter surface of the pipes (typically where the root and hot pass zones of the weld are located). Such focussed transverse waves may be used to systematically test a region of material, irrespective of whether a defect is detected.

The step of detecting radiation from the first, second and third regions resulting from the incidence of the first, second and third beams is preferably performed using one or more of said plurality of ultrasonic transducers. The third region is preferably the same as the first region. The third region may overlap with the first region, and preferably covers the first region.

The first and second beams are preferably emitted substantially contemporaneously. The first and third beams are preferably emitted substantially contemporaneously. The first and third beams of radiation are preferably emitted such that the phased ultrasonic transducer array system is able to distinguish detected radiation resulting from the first beam from radiation resulting from the third beam. The first and third beams of radiation may for example, although emitted substantially contemporaneously, be emitted one after the other with sufficient delay to allow the phased ultrasonic transducer array system to distinguish between detected radiation resulting from the first beam and detected radiation resulting from the third beam. Alternatively, or additionally, the first and third beams of radiation may be emitted in directions such that a reflection of either beam from a defect on the weld would be received by different ultrasonic transducers.

The first, second and third beams may all be emitted substantially contemporaneously. The method may thus be able to perform at least three inspections of the weld at substantially the same time. The information extracted from the detected radiation may be sent to a data processing unit as a multiplexed data signal. Whilst operations may be conducted substantially contemporaneously in the context of the time taken to inspect the entire weld at a given cross-section of the weld, it will be appreciated that the operations, or parts thereof, may be conducted one after the other (for example, with two successive operations being conducted within a time frame of the order of a fraction of milliseconds). The first and third beams may be emitted simultaneously, but focussed on different regions of the weld. All of the first to third beams may be emitted simultaneously, and directed at different regions of the weld.

The incident angle of a beam emitted by the ultrasonic transducers at the boundary between the plurality of ultrasonic transducers and the pipe may be such that both transverse waves and longitudinal waves enter the pipe across the boundary. For example, the incident angle (in this context, measured from the normal axis, such that an incident angle of 0 degrees would be perpendicular to the surface) may be below the first critical angle. The angle of the beam within the pipe may be changed by means of altering the mode of operation of the phased array (for example employing beam steering techniques known in the art and sometimes referred to as focal law techniques). Transverse waves may be converted into longitudinal waves within the pipe material, for example, by means of internal reflection on a boundary. Such longitudinal waves are typically referred to as "mode converted longitudinal waves". Mode converted longitudinal waves have the advantage of carrying more energy than longitudinal waves reflected from an incident longitudinal wave. The first beam is preferably a mode converted longitudinal wave when incident on the first region.

Incidental (i.e. secondary) waves may be present in the case where the first beam is a mode converted longitudinal wave. Such incidental waves typically result from the longitudinal waves emitted when the incident beam is below the first critical angle. If the incidental waves are reflected, for example by a flaw located on the bevel face, then such reflected waves need to be distinguished from reflections of the first beam. The method may therefore include detecting radiation resulting from the third beam. In this sense, the third beam may be used in a "corroborative mode" as a conventional focussed transverse (shear) wave beam simply to confirm whether reflections resulting from the first beam are as a result of reflections caused (a) by a defect located at the position on the bevel face where the mode converted longitudinal waves of the first beam are incident or (b) by a defect located at a position where incidental waves are reflected. In such a case, the third region is preferably the same as the first region.

Preferably, the amplitude of the radiation received as a result of reflection of the mode-converted longitudinal waves from the first beam is used to measure the size of a defect, whereas the third beam is used to confirm that the defect is present at the first region. The method is therefore able to reduce significantly the chance of "false positive" indications being provided. For example, if the third beam suggests that there is no defect at the first region, then any reflected radiation detected that might otherwise be used to size a defect in the first region can be dismissed as a false positive. Such false positive reflections can for example result from incidental radiation emitted when generating the mode-converted longitudinal waves.

Whilst it is preferred in certain embodiments of the invention for the incident angle to be below the first critical angle, the incident angle of the beam relative to the pipe boundary may be such that only transverse (shear) waves enter the pipe across the boundary (i.e. between the first and second critical angles).

As mentioned above, the amplitude of waves reflected from a defect may be measured and then used to provide an accurate measurement of the size of a defect. The size of the defect may be ascertained with surprisingly high accuracy by means of using a look-up table, which correlates the amplitude of the waves detected at a certain position in the weld with the size of the defect. It will be appreciated that the look-up table may be in the form of a formula or one or more graphs, but it is preferred to use a conventional look-up table providing the likely defect size for each of a plurality of different zones of the weld and for each of a plurality of different ranges of reflected amplitude. The look-up table may correlate the amplitude of reflected radiation with defect size on a zone-by-zone basis, there being at least six different zones. The different zones may for example include at least four fill zones, at least one root zone, and at least one cap zone. It will be appreciated that the accuracy of the information provided by the look-up table is increased if the beam of radiation from which the reflection is measured is focussed to be incident on only one zone. If a defect in, or extending to, an adjacent zone affects the amplitude of reflections from radiation used to inspect a particular zone, the method may include a step of taking such affects into account when calculating the size of a defect on the basis of the amplitude of reflected radiation.

The method may include an initial step of creating a look-up table to be used subsequently in calculating the size of a defect from the amplitude of waves reflected from the defect. A separate look-up table may be needed in respect of the particular geometry of the weld/weld bevel. Creating the look-up table may include providing a calibration test-piece with a defect (or simulated defects) of a known size and measuring the amplitude of radiation reflected by such a defect. The defect may be simulated by means of an acoustic reflector. The position and geometry of the acoustic reflector preferably corresponds to the geometry of the weld bevel for forming the real weld between the pipes. Creating the look-up table may include making physical measurements in respect of each zone of the weld bevel. Some values in the look-up table may be calculated by means of interpolation or extrapolation.

There may be a step of emitting a surface wave from one of the plurality of ultrasonic transducers along a first surface of one of the pipe-sections. A surface wave may be utilised to perform a transverse inspection of the outer diameter of the pipes. A surface wave may be utilised to inspect the weld in the region of the weld cap. The surface wave may be in the form of a creeping wave.

The weld may be divided into various "zones" such as for example a cap zone, a root zone, a hot pass zone, one or more fill zones. The zones of the weld may simply be referred to as a "first zone", a "second zone" and so on. The aforesaid "first region", "second region" and "third region" may overlap with one or more such "zones". For example, the "first region" (receiving the first beam) may encompass the "first zone". The "first region" may be the same as the "first zone". The aforesaid "third region" (receiving the third beam) may overlap with, encompass, or be the same as said "second zone". Preferably, the first zone is different from the second zone. Preferably, the first zone does not overlap with the second zone. The first zone may be directly adjacent to the second zone. The method may be performed in such a way as to enable discrimination between separate zones of the weld.

The phased array may for example be driven under a succession of different focal laws, effectively generating ultrasonic beams focussed on one zone only of a plurality of zones of the weld region. Discrimination between zones may permit accurate sizing of defects and reduce false readings, as a positive indication of a defect on one zone and no others provides information concerning the likely size and orientation of the defect in view of the height of the zone and the shape of the zone.

Focussed ultrasonic radiation may be emitted from the phased array to a first zone of the weld and to a second zone of the weld. Radiation transmitted from the first and second zones resulting from the incidence of the emitted radiation on the first and second zones may then be detected with the phased array. The radiation and the phased array are preferably so arranged that it is possible to distinguish between radiation from the first zone and radiation from the second zone.

The method may include a step of extracting time of flight information, which may for example include detecting the time of flight of waves from the root of the weld. Time of flight information may provide an indication of the present or absence of a defect. The method may be performed such that the waves, used in the step of extracting time of flight information from the waves from a defect, are caused by longitudinal waves incident on the defect.

The method preferably utilises a special method of inspection of the root of the weld. It will be appreciated that detection of defects in the weld root is of particular importance and that there may be difficulties with testing for such defects in the root as a result of the position and geometry of the weld and the pipes. The method may include providing at least two different visual representations of NDT inspections of the weld root. Providing two different visual representations of the root enables an operator to better gauge the likelihood of defects in the weld at the root. Providing the two different visual representations may require performing the steps of emitting from one or more of the plurality of ultrasonic transducers a beam of ultrasonic radiation incident on a part of the root of the weld, and detecting with one or more of the plurality of ultrasonic transducers radiation from the root of the weld resulting from the incidence of the beam directed at the root. The two visual representations may be one or more of the following visual representations: A-scan, B-scan, C-scan, D-scan, and S-scan representations. Preferably, at least one of the two visual representations provides amplitude of reflection information. Preferably, at least one of the two visual representations shows a 2-dimensional scan of a part of the weld. The two visual representations are preferably provided simultaneously. The method may include a step of allowing the operator to choose a location in the 2-dimensional representation and then displaying the A-scan information corresponding to that location. The A-scan representation may show a graph of amplitude of acoustic radiation received over time. The 2-dimensional scan representation may show a 2-dimensional map of the weld, with points on the map being coloured according to time-of-flight information and/or peak amplitude received. The two visual representations may consist of an A-scan and a B-scan.

The plurality of ultrasonic transducers may comprise first and second phased ultrasonic transducer arrays. Each array may be provided as a single unit, housing the array of transducers. Each unit may house a plurality of arrays. The arrangement of the phased ultrasonic transducer arrays may be such that a first array is positioned on one side of the weld, whereas a second array is positioned on the opposite side (for example, one array on an upstream side and one array on a downstream side). Some elements of the arrays may be dedicated to transmission. Some elements of the arrays may be dedicated to reception. Some elements of the array may be able to both transmit and detect ultrasonic radiation. Preferably, all elements of the arrays used in the steps of the method of the invention may be used to both transmit and detect ultrasonic radiation.

The method may include a step of detecting ultrasonic radiation with two or more of the transducers operating in a pitch-catch mode. The transducers may be operated in a pitch-catch mode when inspecting for defects in material nearer the region midway between the inner diameter surface and the outer diameter surface of the pipes (for example, fill pass zones of the weld). The method may include a step of detecting ultrasonic radiation with one or more of the transducers operating in a pulse-echo mode. The transducers may be operated in a pulse-echo mode when inspecting for defects on or near the inner diameter surface of the pipes (typically where the root and hot pass zones of the weld are located). The method may include operating at least some of the plurality of ultrasonic transducers in both a pitch-catch mode and a pulse-echo mode. The method may include operating two or more transducers in a pitch-catch mode substantially contemporaneously with operating one or more ultrasonic transducers in a pulse-echo mode.

The method may include a step of emitting from one or more of the plurality of ultrasonic transducers a wide beam of ultrasonic radiation to perform a volumetric scan of the material. Such a volumetric scan may comprise emitting ultrasonic radiation to be incident on a region coinciding with two or more zones. As mentioned above, the second beam may be considered as performing a volumetric scan. A volumetric scan near the cap zone of the weld may be performed by means of the combination of a surface wave and a longitudinal wave. The one or more volumetric scans are preferably performed substantially contemporaneously with the scan using the first beam, that is either at the same time or very shortly before or after.

As mentioned above, the method includes emitting first, second and third beams of ultrasonic radiation. The method may include a step of emitting from one or more of the plurality of ultrasonic transducers a transverse wave beam to inspect the root of the weld. This inspection may be performed by operating one or more of the transducers in pulse-echo mode. This transverse wave beam may be emitted substantially contemporaneously with the first beam, that is at the same time and/or very shortly before or after.

The method may include a step of emitting from one or more of the plurality of ultrasonic transducers a transverse wave beam to inspect the hot pass zone of the weld. This inspection may be performed by operating one or more of the transducers in pulse-echo mode. This transverse wave beam may be emitted substantially contemporaneously with the first beam.

The step of emitting the first beam may be used to inspect a fill zone of the weld by means of a mode converted longitudinal wave. A plurality of further mode converted longitudinal waves may be emitted to inspect a plurality of further fill zones of the weld. These further mode converted longitudinal waves may be emitted substantially contemporaneously with the first beam.

The step of emitting the third beam may be used to inspect a fill zone of the weld by means of a transverse wave. A plurality of further transverse waves may be emitted to inspect a plurality of further fill zones of the weld. These further transverse waves may be emitted substantially contemporaneously with the third beam.

The inspection of fill zones is conveniently performed by operating two or more of the transducers in pitch-catch mode.

The method may include a step of emitting from one or more of the plurality of ultrasonic transducers a transverse wave beam to inspect the cap zone of the weld. This transverse wave beam may be emitted substantially contemporaneously with the first beam. The cap zone may substantially contemporaneously also be inspected by means of a mode converted longitudinal wave. Inspection of the cap may be performed by operating one or more of the transducers in pulse-echo mode.

The method may include a step of emitting from a dedicated ultrasonic transducer on one side of the weld a longitudinal wave beam to be reflected from the internal diameter of the pipe to be detected by a dedicated ultrasonic transducer on the opposite side of the weld, thus performing a transverse inspection of the internal diameter. This inspection of the internal diameter may be performed substantially contemporaneously with the scan using the first beam.

The method may include a step of emitting from a dedicated ultrasonic transducer on one side of the weld a transverse wave beam to be reflected via the internal diameter as a longitudinal wave onto the external diameter of the pipe, the radiation being detected by a dedicated ultrasonic transducer on the opposite side of the weld, thus performing a transverse inspection of the external diameter. This inspection of the external diameter may be performed substantially contemporaneously with the scan using the first beam.

A transverse inspection may enable detection of a flaw arranged perpendicularly orientated to the direction of welding. The transverse inspection of the internal and/or the external diameter may involve inspecting a region of the weld that is circumferentially separated (lies in a different sector of the pipe) from the dedicated transducers that perform the inspection. The beams of radiation from the dedicated transducers may thus be along directions that are not coplanar with the axis of the pipes, unlike other beams of radiation used in the scans.

As mentioned above, the plurality of ultrasonic transducers may comprise a first phased array and a second phased array. The plurality of ultrasonic transducers may comprise a first ultrasonic transducer separate from the first phased array and a second ultrasonic transducer separate from the second phased array. The first ultrasonic transducer may be in the form of the dedicated ultrasonic transducer mentioned above. The method may include a step of emitting from the first ultrasonic transducer a beam of ultrasonic radiation which is then detected by the second ultrasonic transducer. The beam of ultrasonic radiation emitted by the first ultrasonic transducer may be emitted along the first surface. Alternatively the beam may be internally reflected by a surface of the pipe. The dedicated beam of ultrasonic radiation emitted by the first (e.g. dedicated) ultrasonic transducer may be emitted substantially contemporaneously with the emission by the first phased ultrasonic transducer array of said first beam of ultrasonic radiation.

The method may include a step of emitting from one or more of the plurality of ultrasonic transducers fourth, fifth and sixth beams of ultrasonic radiation and then detecting radiation resulting from any of the fourth, fifth and sixth to provide an indication from which the likelihood of a defect in the weld may be discerned. The fourth, fifth and sixth beams of ultrasonic radiation may be emitted substantially contemporaneously with the emission of the first beam of ultrasonic radiation. Each of the fourth, fifth and sixth beams of ultrasonic radiation may be in the form of any of the beams of radiation mentioned herein, provided that the beams are all different in terms of the type of beam emitted or the region of the weld being inspected. For example, the first and third beams may be used to inspect a first fill zone, the second beam may be used to inspect a cap zone, the fourth and fifth beams may be in the form of a mode-converted longitudinal wave beam and a corroborative shear wave beam used to detect defects in a second fill zone, and the sixth beam may be used to detect defects in the root zone.

The step of providing an indication from which the likelihood of a defect in the weld may be discerned may include providing the location of a defect. The size of the defect may additionally, or alternatively, be provided. The indications provided concerning the defect may be derived solely from ultrasound measurements. Thus, additional NDT methods need not be employed in order to properly categorise the defects detected. The indication from which the likelihood of a defect in the weld may be discerned may be in the form of a visual indication. The indication may include a calculated dimension of the defect. The indication may include a calculated position of the defect. The indication may be displayed on a visual display unit.

The method of the present invention has particular application when the pipes are pipes clad with a corrosion resistant alloy (CRA). The CRA may be in the form of stainless steel or a nickel alloy, for example. The material to be welded may therefore comprise austenitic material. The weld may therefore be considered as being an austenitic weld, in that the material welded together and/or the material in the heat-affected zone comprises austenitic material. The pipes may be carbon steel pipes clad with CRA, for example metallurgically bonded with CRA. The principles of the present invention may be applied to welds other than austenitic welds, but the described embodiments of the invention are of greater advantage when applied to austenitic welds.

The pipelines may be underwater pipelines or inland pipelines. The method of the present invention has particular application however when the pipes are being welded together during a method of laying an underwater pipeline. The pipeline may for example be a gas or oil pipeline.

The weld may be inspected by means of inspecting successive segments (effectively thick cross-sections) of the weld joint. Each segment (or notional segment) of the weld may be in the form of a generally wedge-shaped section of the pipes and weld material, the wedge-shaped section extending from a thin end at the internal diameter of the pipes to a thicker end at the outer diameter. The notional wedge-shaped section conveniently has a shape that encompasses (and is aligned with) a cross-section of the weld, the section being taken along a plane that contains the longitudinal axis of the pipes and a radius of the pipes. Each segment may be inspected in turn by means of moving the phased array(s) in a circumferential direction around the pipes. All the ultrasonic NDT may be conducted in the time it takes the phased array(s) to perform a single revolution around the pipes. The whole weld (which has an annular shape of course) may be analysing by means of scanning a sufficient number of successive overlapping wedge-shaped segments of the weld joint. The speed of movement around the pipes may be greater than 10 mms$^{-1}$. The speed of movement around the pipes may be greater than 25 mms$^{-1}$. The speed of movement around the pipes may be less than 250 mms$^{-1}$. The plurality of ultrasonic transducers may also comprise further ultrasonic probes not forming part of a phased probe array.

The present invention also provides an apparatus for performing the method of the invention. The apparatus may comprise a phased ultrasonic transducer array system. The apparatus may additionally comprise one or more ultrasonic transducers that do not form part of a phased array. The apparatus may comprise a control system. The control system may be configured to control the ultrasonic transducers to operate in accordance with any aspect of the method of the invention as described or claimed herein. The control system may comprise a means for outputting a signal which causes a phased array to emit a beam of radiation. The means for outputting a signal may be able to output a signal which controls one or more characteristics of the ultrasonic beam thus emitted. The characteristics of the ultrasonic beam may for example include direction, focus, duration, intensity, and shape of waveform. The control system may comprise a means for controlling the detection of ultrasonic radiation. The control system may comprise a processing unit for processing electronic signals generated by ultrasonic transducer elements of the phased ultrasonic transducer array system on detection of ultrasonic radiation. The processing unit may be arranged to output signals which are then used to produce the indication from which the likelihood of a defect in the weld may be discerned.

The apparatus may additionally comprise one or more welding torches to weld the pipes together.

The apparatus may include a display apparatus, such as a visual display unit, for displaying an indication from which the likelihood of a defect in the weld may be discerned.

The present invention also provides a method of creating a look-up table, for use in a method according to any aspect of the invention described or claimed herein where a look-up table is used to correlate amplitude of detected ultrasonic radiation with a size of defect. Such a method may include ascertaining a particular geometry of weld, having a particular bevel geometry split into a plurality of different zones. The method includes correlating amplitudes of ultrasonic radiation with defect sizes. The method may be performed by means of mathematical modelling or computer simulation. The method may include providing a calibration test-piece. The method may include emitting from one or more of a plurality of ultrasonic transducers a beam of ultrasonic radiation incident on a region of the test-piece and measuring the reflected radiation. There may be steps of measuring the amplitude of reflected radiation from one or more acoustic reflectors having a known size located in such a calibration test-piece. The test-piece and one or more acoustic reflectors preferably have a geometry corresponding to the bevel geometry so as to give representative amplitude measurements for use in the look-up table. The look-up table may correlate the amplitude of reflected radiation with defect size on a zone-by-zone basis, there being at least six different zones.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which:

FIG. 1b is a cross-sectional view of the pipes shown in FIG. 1a, taken along the lines B-B in FIG. 1a;

DETAILED DESCRIPTION

The presently described embodiments of the invention concern the detection of defects in the region of a weld-joint between two pipes, during a method of laying an underwater pipeline from a floating vessel. The pipeline is laid overboard a vessel by welding successive sections of pipe to the end of the pipeline. When laying a pipeline, the tension in the pipeline being laid is significant and is typically of the order of several hundreds of kilo-Newtons. During laying and/or subsequent use of the pipeline, the pipe joints may be subject to fatigue loading. It is therefore of particular importance to ensure that the joints between the sections of pipe that make up the pipeline are of a very high quality. Failure of any joint in the pipeline after the joint has been lowered from the vessel into the water can be extremely costly and possibly dangerous. The present embodiments concern testing the integrity of a pipe joint by means of an ultrasonic-radiation-based non-destructive testing system.

Figure 1A:
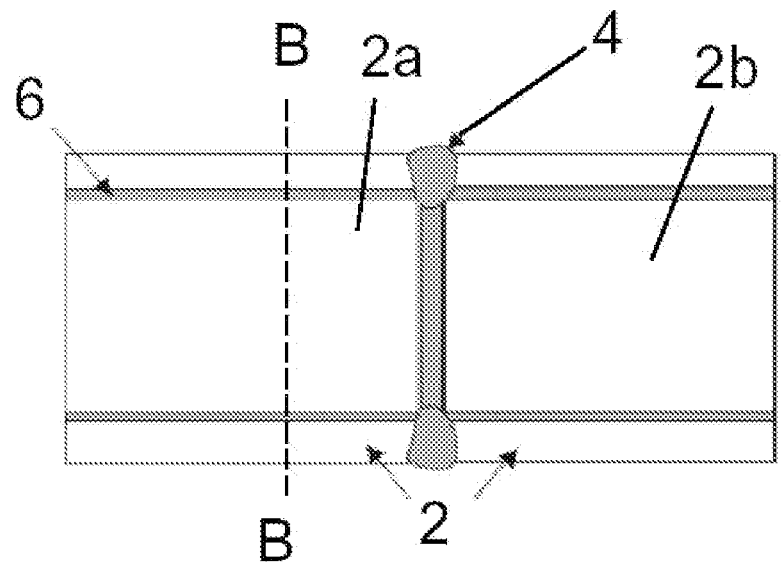
FIG. 1a is a longitudinal cross-sectional view of two pipes that have been welded together.
Figure 1B:
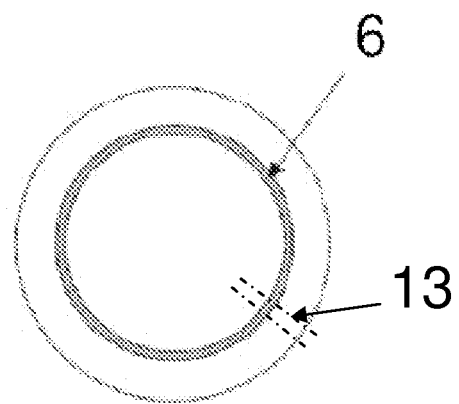

FIG. 1a shows two pipe sections 2 in longitudinal cross-section. There is a first pipe section 2a connected to a second pipe section 2b by means of a weld 4. The pipe sections are carbon steel pipes internally clad with a corrosion resistant alloy (CRA) 6 (FIG. 1b), which in this case is in the form of a nickel alloy, but could also be stainless steel or other CRA materials. The CRA material has an austenitic grain structure. The weld 4 is formed by means of a plurality of GMAW (gas metal arc welding) torches operating in a manner well known in the art. The weld 4 is in the form of a girth weld, and because it joins two pipes partially formed of austenitic material is referred to herein as an austenitic weld.

Figure 2:
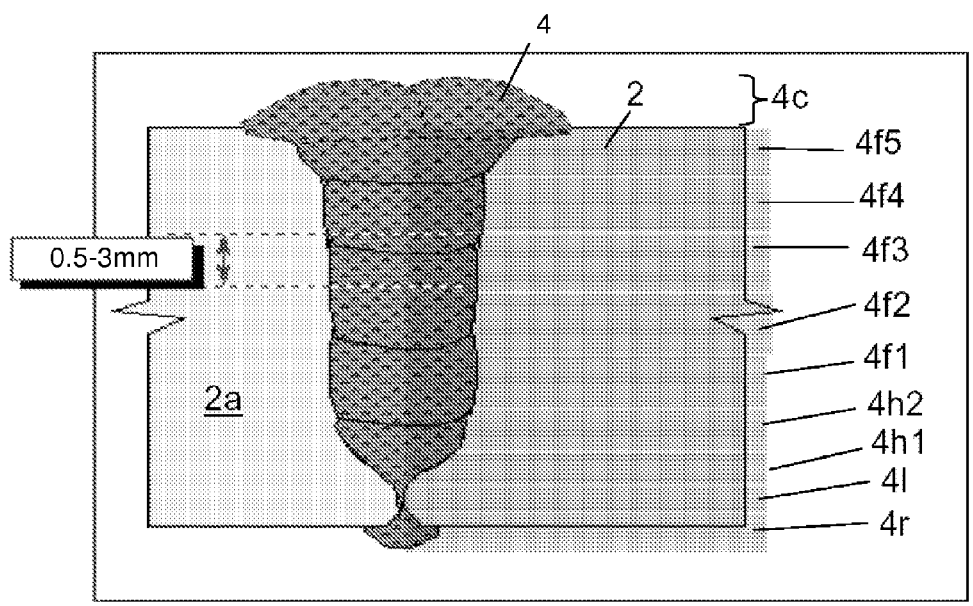
FIG. 2 is a longitudinal cross-section of the weld-joint between the two pipes.
Figure 3:
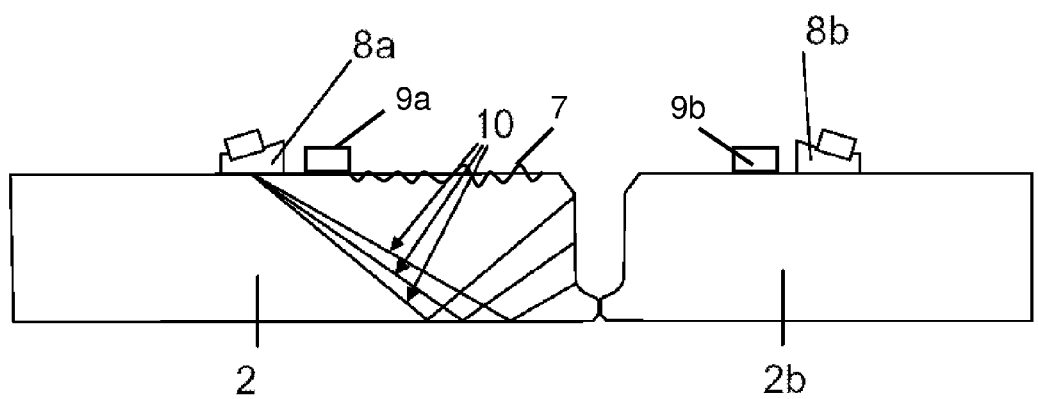
FIG. 3 is a partial longitudinal cross-sectional view showing ultrasonic transducers arranged on the outer wall of one of the pipes for testing the weld in accordance with an NDT method of a first embodiment.

FIG. 2 shows the weld 4 between the two pipes 2 in greater detail. The weld 4 is formed by means of welding torches depositing separate layers of weld material in the region between the two pipes 2a, 2b. The pipes are bevelled prior to being joined to create a gap between the pipes 2. Different bevel shapes are well known in the art. The bevel shape utilised in the present case is one where the sides of the weld-joint to be formed, defined by the opposing ends of the pipes, are close to parallel for the majority of the depth of the weld-joint. A schematic illustration of the shape of the bevel (before welding) is shown in FIG. 3. In FIG. 2, the various layers of the weld joint, after welding, are shown. The weld joint comprises a root zone 4r, an LCP zone 4l (that zone where the pipes in an unwelded joint touch each other, LOP standing for lack of cross penetration), two hot pass zones 4h1, 4h2, five fill zones 4f1 to 4f5, and a weld cap zone 4c. As a rough indication of scale, each fill zone 4f has a depth which is typically of the order of 0.5 to 3 mm.

The method of non-destructive testing of the weld is performed solely by means of inspecting the weld joint with ultrasonic probes. An NOT method according to a first embodiment of the invention will now be described with reference to FIG. 3.

FIG. 3 shows two ultrasonic transducer arrays 8a, 8b used in the NDT method. The arrays 8a, 8b are arranged on the pipe sections 2 on opposite sides of the weld joint. Each array is in the form of a 90 mm phased array R/D Tech probe available from Olympus Corporation. The arrays operate at a frequency of about 4 MHz and are provided with a rexolyte wedge having an angle of about 21°. Each phased array unit 8a, 8b has two banks of 30 transducer elements. Thus with two phased array units 8a, 8b there are a total of 120 transducer elements, 60 upstream of the weld joint and 60 downstream. In addition to the phased array probes 8a, 8b there is also mounted ultrasonic probes 9a and 9b dedicated to generating surface waves 7. A further set of ultrasonic probes may also be used to detect transverse defects within the weld (not shown). All of the probes are mounted for movement together in the circumferential direction around the pipes 2, so that the entire girth weld may be inspected in one revolution, with overlap between start and finish of the revolution to ensure complete inspection of the weld. The weld is inspected by means of inspecting successive segments (effectively thick cross-sections) of the weld joint. Each segment (or notional segment) of the weld may be in the form of a generally wedge-shaped section of the pipes and weld material. Such a notional wedge-shaped section is illustrated highly schematically in FIG. 1b by means of the broken lines 13 which encompass a cross-section of the weld taken along a plane that contains both the longitudinal axis of the pipes and a radius of the pipes. FIG. 2 is an example of such a cross-section. An encoder associated with the transducer assembly enables the apparatus to ascertain where along the circumference the transducer array is inspecting.

During performance of the weld inspecting method, the phased array units 8a, 8b are operated in accordance with a sequence of focal laws which cause the transducers of the array to create beams of ultrasonic sound radiation at a variety of different angles. These beams may be received at the same angle as they are generated (pulse-echo configuration) or at a different angle (pitch-catch/tandem configuration where the beams are emitted and received at different positions—in this embodiment the emitter and detector when operating in pitch-catch mode are provided by different transducers on the same phased array and are thus on the same side of the weld joint).

FIG. 3 shows schematically three beams 10 of shear (transverse) wave ultrasonic radiation emitted from one 8a of the phased arrays at different angles, thus being directed at different zones of the weld. At the same time, focussed shear wave beams (not shown in FIG. 3) are emitted from the same phased array 8a, subsequently being mode converted to compression (longitudinal) waves which are received at the same zones of the weld. By this means, beams of both shear wave and compression wave ultrasonic radiation are transmitted to each of the zones of the weld shown in FIG. 2. At the same time, dedicated probes 9a, 9b emit beams of surface waves 7 which travel along the outer diameter of the pipes 2, which are incident on the weld as a compression wave. The beams 10 of radiation are emitted in sequence, the progression of the sequence being sufficiently fast that the movement of the array units 8a, 8b around the circumference of the pipes 2 is negligible.

Thus, the beams emitted by one set of transducers 8a, 9a include a first focussed beam of ultrasonic radiation incident on the weld as a mode-converted compression (longitudinal) wave (the waves not shown in FIG. 3), a second surface wave beam 7 of ultrasonic radiation also incident on the weld as a compression wave, and a third focussed beam (any of beams 10 shown in FIG. 3) of ultrasonic radiation incident on the weld as a shear wave. The first, second and third beams are emitted quickly in succession, possibly with other beams of radiation (such as the other shear waves 10 and the other mode-converted compression waves not shown in FIG. 3) being emitted and detected at the same time or between emitting the first to third beams. The cycle of emitting/detecting radiation is sufficiently quick that the first, second and third beams can be considered as being emitted substantially contemporaneously.

As a result of emitting the beams of radiation (including beams 10 in FIG. 3), as focused beams on successive zones of the weld at successive times, it is possible for the NDT system to distinguish between radiation received as a result of emitting radiation to one zone from that of radiation received as a result of emitting ultrasonic radiation to a different zone of the weld. The ultrasonic radiation is, in the modes of operation used in the present embodiment, detected by the same phased array unit 8a, 8b that emits the radiation. The detection of ultrasonic radiation from the weld-joint results in the extraction of time of flight information, which indicates the location of the origin of the radiation, and amplitude information, which indicates the presence and size of a flaw. Because the system is able to distinguish between zones of the weld, such information is extracted on a zone-by-zone basis. Such information is then correlated by a processor of a control unit (not shown) and displayed on a visual display unit (not shown) from which an operator may readily see whether or not a defect exists in the weld, and if it does, where it is located. Defect size information may be presented on detection of a defect by correlating the size of the amplitude of reflection with the defect size on a zone-by-zone basis. The present embodiment scans the entire girth weld 4 by means of successive individual NDT operations that are executed quickly one after the other in a cyclic fashion. As a result of the speed of cycling these operations, the operations can be considered as being performed substantially contemporaneously.

Different zones of the weld may be inspected by means of different ultrasonic testing operations, including using scans similar to the scans performed by the first second and third beams mentioned above. The table below shows the NDT operations that are performed during each cycle in accordance with the present embodiment:

TABLE A

NDT Operations performed-summary

| Zones | Beam configuration | Probes |
| --- | --- | --- |
| Root | TW – Pulse – Echo | Phased Array |
| Hot Pass | TW – Pulse – Echo | Phased Array |
| Fill Zones | TLLW – Pitch – Catch + TW | Phased Array |
| Cap | TW + TLW – Pulse – Echo | Phased Array |
| Volumetrics | LW – Half Skip | Phased Array |
| Cap Mapping | Surface Wave | Dedicated probes |
| Root Mapping | TW – Half Skip | Phased Array |
| TOFD on Root | TW Pitch – Catch | Dedicated Probes |
| Transverse OD | Surface Wave | Dedicated Probes |
| Transverse ID | LW – Pitch – Catch | Dedicated Probes |

In Table A, the abbreviations TW, TLW, TLLW and LW are used. "TW" stands for transverse wave (shear wave). "TLW" stands for transverse=>longitudinal waves. In TLW operations, a transverse (shear) wave internally reflected on the inner diameter wall of the pipe mode-converts into a longitudinal wave, which is then reflected on a flaw back along the same path to be detected as a transverse wave. "TLLW" stands for transverse=>longitudinal→longitudinal waves. In TLLW operations, a transverse (shear) wave internally reflected on the inner diameter wall of the pipe mode-converts into a longitudinal wave, which is then reflected on a flaw as a longitudinal wave back along a different path to be detected as a longitudinal wave. "LW" stands for longitudinal wave.

It will be seen that for some zones, shear waves (transverse waves) are used to detect defects in any area of a given zone. Such shear waves may be converted into compression (longitudinal) waves by means of reflection within the pipe 2. Such mode-converted compression waves are, for some zones, used to detect defects in any area of a given zone. In addition, surface waves are used to detect defects on the outer diameter of the pipe, and wide-beam compression waves are used to detect defects in the volume of the weld material (as opposed to on the bevel faces).

It will be seen that volumetric scans of the weld are also performed. These scans include a volumetric inspection of the fill layers by means of three separate, successive, half skip wide-beam longitudinal (compression) waves directed at different regions of the weld. Each volumetric scan includes emitting ultrasonic radiation which is incident on a region coinciding with two or more fill layer zones. The longitudinal waves are produced directly by the transducers (and are not mode-converted). From these volumetric scans, information can be extracted concerning the depth of a detected defect from the outer diameter and the length of a defect (using the 6 dB method). A further volumetric scan is also performed near the cap zone of the weld by means of the combination of a surface wave and a wide beam longitudinal wave.

The following three types of scan are performed: (i) the root and/or hot pass scan in pulse-echo mode using transverse waves, (ii) the fill zones in pitch-catch mode using mode-converted longitudinal waves with transverse waves for corroboration, and (iii) a scan of the cap, which may be in the form of surface wave scans or part of a volumetric scan of the weld. Performing those three types of scan with one apparatus has been found to be particularly advantageous. Mode converted longitudinal waves have good propagation properties. Combining such mode converted longitudinal waves with shear wave techniques and surface waves enables 100% of the girth weld to be inspected to the standard required in fatigue sensitive welds, such as steel catenary risers. Emitting shear waves and compression waves substantially contemporaneously improves speed and efficiency.

The scans of the root include scans by the transducer array by means of shear wave scans for defects in pulse-echo mode, root-mapping using shear wave scans in half-skip pulse-echo mode, time-of-flight-diffraction measurements using shear waves in pitch-catch mode and scans by the dedicated transducers by means of transverse inspection of the outer diameter with surface waves and transverse inspection of the inner diameter with longitudinal waves in pitch-catch mode. The aforementioned scans of the root may be converted into visual representations for the user. Preferably, a 2-dimensional representation of the weld root is produced together with an A-scan. An A-scan may provide useful extra information for the operator to analyse in the case where the 2-D scan, which may be a B-scan, suggests the presence of a defect in the root. The 2-D scan may represent the entire bevel face in the region of the root (i.e. around the circumference). Alternatively, the 2-D scan may represent the porosity of the weld in the region of the root. The operator is able to select which point in the 2-D image he wishes to obtain the A-scan information.

By means of the above embodiment, NDT testing of the whole weld, including in particular the root, may be performed without needing additional visual checks.

Figure 4A:
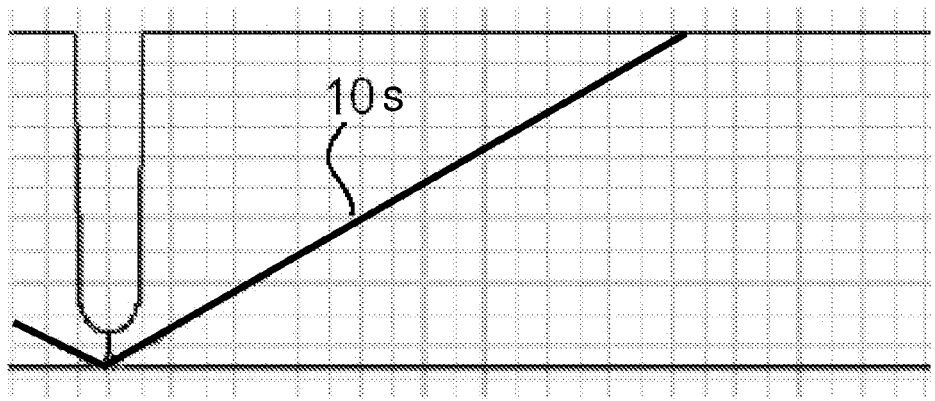
FIGS. 4a to 4h are schematic partial cross-sectional views showing the ultrasonic inspection of various different regions of a weld tested in accordance with an NDT method of a second embodiment.
Figure 4B:
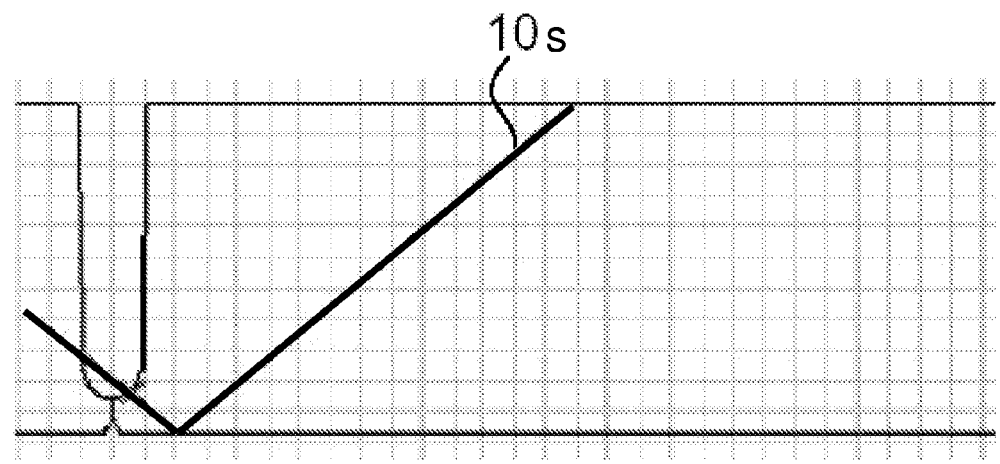
Figure 4C:
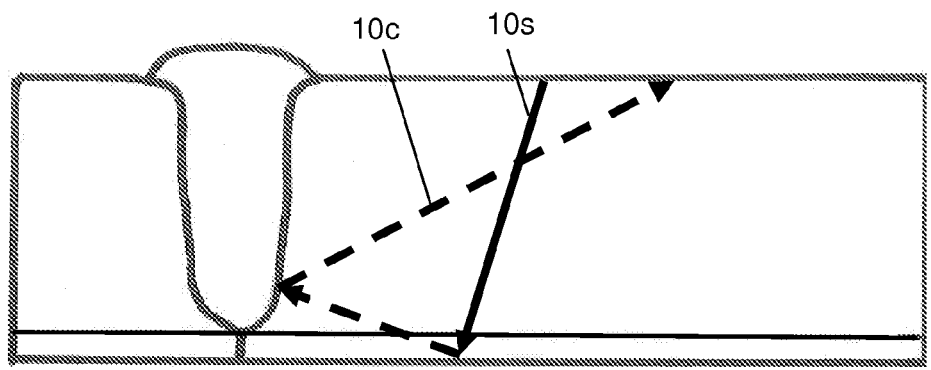

FIGS. 4a to 4h show the various orientations and types of the ultrasonic beams 10 during the various tests on different zones of the weld in a method performed in accordance with a second embodiment of the invention (similar in many respects to the first embodiment). Thus, FIG. 4a shows a pulse echo inspection of the root in which shear waves 10s are generated and received at the same angle by the phased array probes 8a, 8b. FIG. 4b shows pulse echo inspection of the hot pass zone using shear waves 10s. In this case the shear waves reflect off the inner diameter of the pipe before encountering the weld. Any radiation reflecting off a defect on the bevel face would follow the same path in reverse. FIGS. 4c and d show a tandem inspection of the first fill layer using mode-converted longitudinal (compression) waves. FIG. 4c shows the beam used for inspection, which is known as the primary beam. This primary beam is generated by each phased array probe 8a, 8b as a shear wave 10s and is then converted into a compression wave 10c at the inner diameter pipe-air boundary. The compression wave 10c is then reflected back to one of the phased array probes 8a, 8b where its time of flight and amplitude are detected.

Figure 4D:
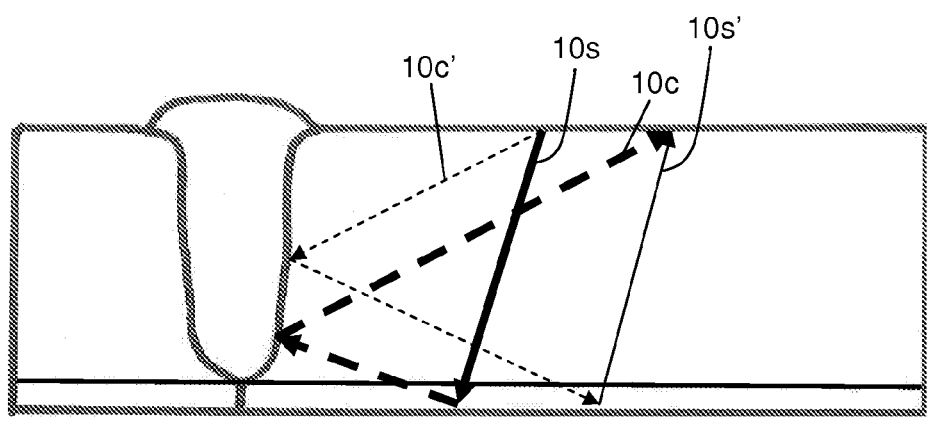

Shear wave 10s must be generated at an angle that means it will be mode converted at the inner diameter of the pipe, specifically at an angle less than the first critical angle. This means than that a secondary beam of compression waves $10c'$ will also be generated incidentally, as shown in FIG. 4d. This secondary (incidental) compression wave is mode converted into a shear wave $10s'$ at the inner diameter pipe-air boundary and encounters the weld at a different region to the primary beam. For this case, signals received by the phased array probes as a result of reflection of the primary beam off a defect on the weld must be distinguished from reflection of the secondary beam off a defect (at a different region) on the weld. Thus, a corroborative scan is employed by means of a shear wave only path (FIG. 4e) in order to confirm that a reflection is from the primary beam or an incidental reflection from the secondary beam incidentally produced (i.e. establishing with certainty the through-thickness position of the flaw).

Figure 4E:
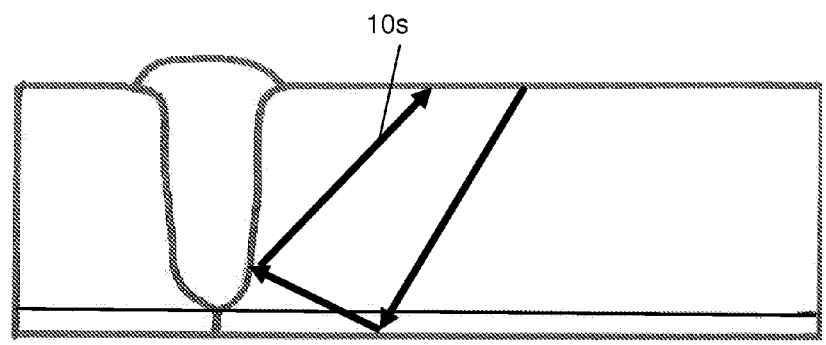

FIG. 4e shows a tandem inspection of the first fill layer using shear waves 10s. In this case the shear waves 10s are generated at an angle greater than the first critical angle so no longitudinal waves travelling through the thickness are produced and the shear waves do not get mode-converted at the inner diameter of the pipe. It will be appreciated that the measurements made by means of the mode-converted longitudinal waves shown in FIGS. 4c and 4d are used to accurately size a defect whilst the shear wave measurements shown in FIG. 4e are made primarily to confirm the position of the defect (and to lessen the chance of false positives).

The inspections shown in FIGS. 4c-e are conducted contemporaneously with each other and furthermore are conducted on all of the fill zones 4/1-4/5 substantially simultaneously by having a small subset of the available phased array elements directed to emitting and receiving radiation from each zone.

Figure 4F:
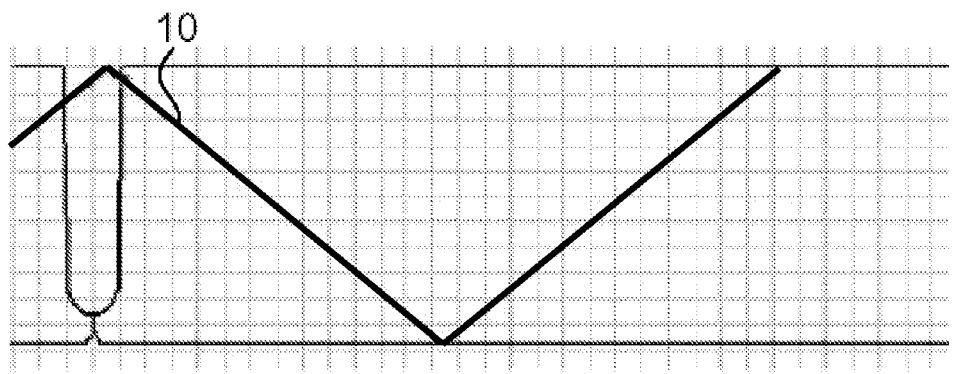
Figure 4G:
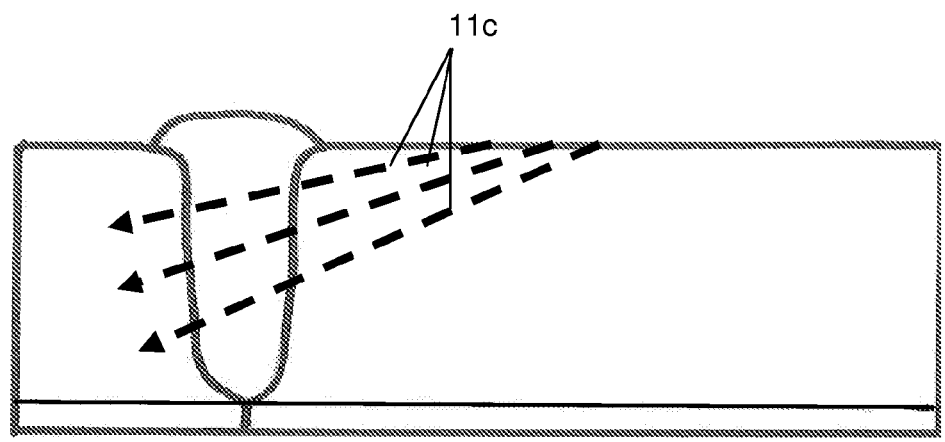
Figure 4H:
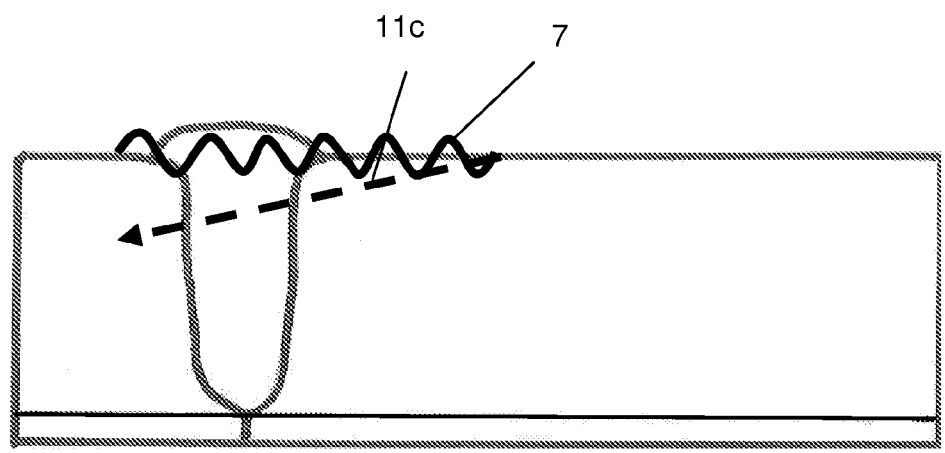

FIG. 4f shows a pulse echo inspection of the cap layer using shear waves. Mode-converted compression waves may be used to inspect the cap in addition to shear waves to confirm the presence and size of any defects detected. The volumetric inspections of the weld are performed by three separate half skip inspections using wide-beam longitudinal (compression) waves 11c, as shown in FIG. 4g. For volumetric inspection of the topmost zones of the weld, both wide-beam longitudinal waves 11c and surface waves 7 may be used, as is shown in FIG. 4h. In addition, dedicated transversely arranged ultrasonic transducer probes (not shown) are provided for inspecting the internal diameter for transverse flaws. Transverse flaw inspection are made for all regions of the weld, but simply separated into two areas, namely the lower and upper parts of the weld. A pair of probes are provided for the transverse flaw inspection of each of the upper and lower parts, being arranged to perform in the pitch catch mode from each side of the weld.

In each case the size of the defect may be determined by analysis of the echo amplitude of the reflection by the defect, given that the signal strength of the reflected signal is an indication of the size and the orientation of the defect.

A time of flight diffraction (TOFD) technique is focused on the root utilising a compression wave. Further information concerning the TOFD methodology employed can be found in the booklet entitled "Back to Basics—Ultrasonics" by John C Drury, published in Insight Magazine in 2004/2005.

The pulse echo mode is used to scan the regions near the boundaries of the pipe at the inner and outer diameters (ID and OD) such as the root, hot pass and cap zones, whereas the pitch-catch mode is used in relation to the fill layers. A volumetric scan utilises wide beam longitudinal (compression) waves generated directly by the phased array probes 8a, 8b to provide information concerning the porosity of the weld.

In this second embodiment, the pipe has a diameter of about 300 mm, a wall thickness of about 22 mm+3 mm (cladding), and a bevel angle of about 8 degrees to the vertical.

The second embodiment utilises 126 transducer elements, 63 arranged upstream and 63 arranged downstream. Of those elements six individual transducer elements are provided (three upstream and three downstream) separately from the upstream and downstream phased arrays, which are each provided by 60 elements. The transducer elements scan the weld and produce measurements on about 50 separate measurement channels. The elements of the phased arrays are able, by means of operating under different focal laws, to emit ultrasonic beams at angles varying from 45 to 70 degrees (in this case the angle being 90 degrees when perpendicular to the surface and 0 degrees when parallel). Surface waves are also able to be transmitted. For non-surface wave inspections, the path length of the radiation may range from about 10 mm to about 90 mm, depending on the measurement being made. (Different path lengths would of course apply in relation to different geometries and sizes of pipe.)

Between about 16 and about 20 elements may be active for any given measurement channel. The elements within a group used to transmit radiation may be the same as the elements used to receive radiation. For some channels, 8 elements are used to transmit and a different 8 elements are used to receive. A series of different measurements, much like those set out in Table A above (relating to the first embodiment) are conducted, each channel being dedicated to a particular type of measurement. For example, one channel may relate to scanning a region of the root by means of a group of elements used in both transmit and received mode, by means of a pulse-echo shear-wave measurement at an angle of 60 degrees with a path length of 52 mm).

The following comments apply to both the first and the second illustrated embodiments.

As mentioned above, the phased array units 8a, 8b move together around the circumference of the pipes 2 so that the entire weld-joint is scanned and analysed following a single rotation around the pipes 2. Both phased arrays scan the joint at the same time. The speed of movement around the circumference is about 70 mm per second, but may be between 50 and 100 mm per second, or other speeds.

It will be appreciated of course that the regions inspected by the phased array units 8a, 8b include not only the weld material but also the heat affected zone adjacent to the weld.

Embodiments of the present invention have been found to be capable of detecting flaws of small dimension (of the order of 0.3 mm) and accurately sizing them. The embodiments also have other advantages. There is no need to conduct supplementary methods of inspection, such as cameras equipped with lasers for internal visual inspection of root.

and then assuming an approximately linear relationship between the amplitude of reflection and the size of the defect. Table B below shows the look-up table produced for the calibration block shown in FIG. 5.

TABLE B

Look-up table for defect sizing

| Corrected | Zone | | | | | | | | | | | |
|---|---|---|---|---|---|---|---|---|---|---|---|---|
| | RT1 | RT2 | HP | 1 | 2 | 3 | 4 | 5 | 6 | 6 | 6 | 6 |
| | | | | | | Height | | | | | | |
| % FSH | 2.0 | 2.8 | 2.4 | 2.4 | 2.4 | 2.4 | 2.4 | 2.4 | 2.4 | 2.4 | 1.5 | 3.0 |
| Amplitude | RT1 | RT2 | HP | F1 | F2 | F3 | F4 | F5 | F6 | F7 | CN1 | CN2 |
| 5 | 0.1 | 0.1 | 0.1 | 0.1 | 0.1 | 0.1 | 0.1 | 0.1 | 0.1 | 0.1 | 0.1 | 0.2 |
| 10 | 0.2 | 0.3 | 0.2 | 0.2 | 0.2 | 0.2 | 0.2 | 0.2 | 0.2 | 0.2 | 0.2 | 0.3 |
| 15 | 0.3 | 0.4 | 0.4 | 0.4 | 0.4 | 0.4 | 0.4 | 0.4 | 0.4 | 0.4 | 0.2 | 0.5 |
| 20 | 0.4 | 0.6 | 0.5 | 0.5 | 0.5 | 0.5 | 0.5 | 0.5 | 0.5 | 0.5 | 0.3 | 0.6 |
| 25 | 0.5 | 0.7 | 0.6 | 0.6 | 0.6 | 0.6 | 0.6 | 0.6 | 0.6 | 0.6 | 0.4 | 0.8 |
| 30 | 0.6 | 0.8 | 0.7 | 0.7 | 0.7 | 0.7 | 0.7 | 0.7 | 0.7 | 0.7 | 0.5 | 0.9 |
| 35 | 0.7 | 1.0 | 0.8 | 0.8 | 0.8 | 0.8 | 0.8 | 0.8 | 0.8 | 0.8 | 0.5 | 1.1 |
| 40 | 0.8 | 1.1 | 1.0 | 1.0 | 1.0 | 1.0 | 1.0 | 1.0 | 1.0 | 1.0 | 0.6 | 1.2 |
| 45 | 0.9 | 1.3 | 1.1 | 1.1 | 1.1 | 1.1 | 1.1 | 1.1 | 1.1 | 1.1 | 0.7 | 1.4 |
| 50 | 1.0 | 1.4 | 1.2 | 1.2 | 1.2 | 1.2 | 1.2 | 1.2 | 1.2 | 1.2 | 0.8 | 1.5 |
| 55 | 1.1 | 1.5 | 1.3 | 1.3 | 1.3 | 1.3 | 1.3 | 1.3 | 1.3 | 1.3 | 0.8 | 1.7 |
| 60 | 1.2 | 1.7 | 1.4 | 1.4 | 1.4 | 1.4 | 1.4 | 1.4 | 1.4 | 1.4 | 0.9 | 1.8 |
| 65 | 1.3 | 1.8 | 1.6 | 1.6 | 1.6 | 1.6 | 1.6 | 1.6 | 1.6 | 1.6 | 1.0 | 2.0 |
| 70 | 1.4 | 2.0 | 1.7 | 1.7 | 1.7 | 1.7 | 1.7 | 1.7 | 1.7 | 1.7 | 1.1 | 2.1 |
| 75 | 1.5 | 2.1 | 1.8 | 1.8 | 1.8 | 1.8 | 1.8 | 1.8 | 1.8 | 1.8 | 1.1 | 2.3 |
| 80 | 1.6 | 2.2 | 1.9 | 1.9 | 1.9 | 1.9 | 1.9 | 1.9 | 1.9 | 1.9 | 1.2 | 2.4 |
| 85 | 1.7 | 2.4 | 2.0 | 2.0 | 2.0 | 2.0 | 2.0 | 2.0 | 2.0 | 2.0 | 1.3 | 2.6 |
| 90 | 1.8 | 2.5 | 2.2 | 2.2 | 2.2 | 2.2 | 2.2 | 2.2 | 2.2 | 2.2 | 1.4 | 2.7 |
| 95 | 1.9 | 2.7 | 2.3 | 2.3 | 2.3 | 2.3 | 2.3 | 2.3 | 2.3 | 2.3 | 1.4 | 2.9 |
| 100 | 2.0 | 2.8 | 2.4 | 2.4 | 2.4 | 2.4 | 2.4 | 2.4 | 2.4 | 2.4 | 1.5 | 3.0 |

During offshore operations, being able to avoid having such supplementary visual inspection methods has a huge impact in terms of cycle time. The small number of ultrasonic probe units used in the present embodiments is advantageous, in that there are lower risks of breakdown.

Figure 5:
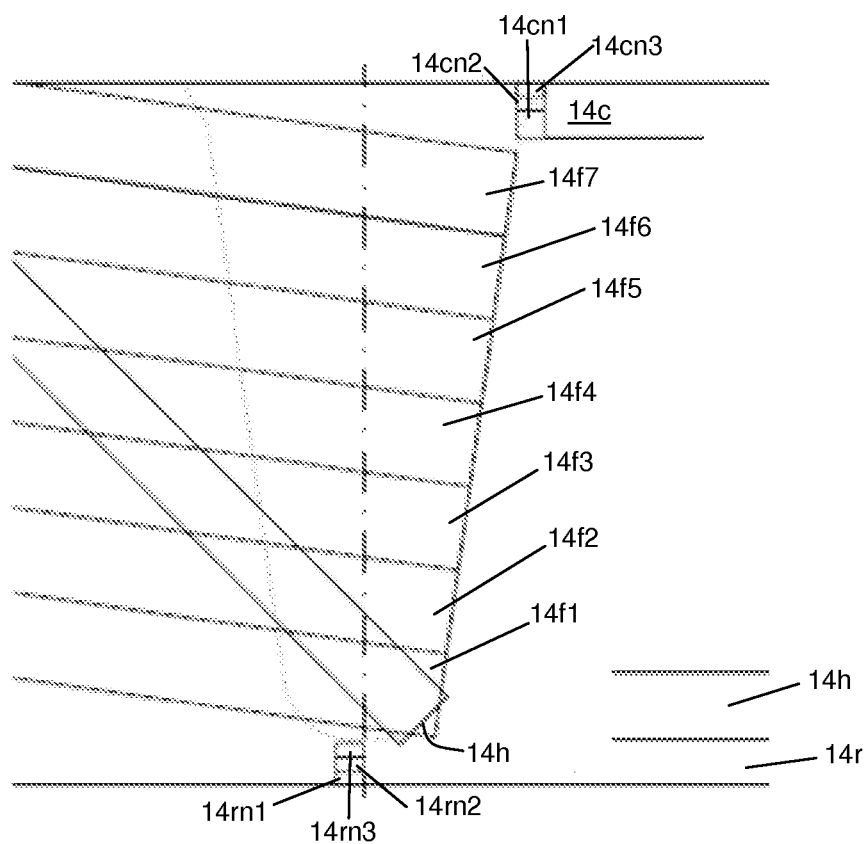
FIG. 5 is a schematic cross-sectional view of a calibration test-piece according to a third embodiment.

FIG. 5 shows a calibration block for use in a third embodiment of the invention. The block includes machined holes at the bottom of each of which there is a flat bottomed hole. The face of the flat bottomed hole is aligned with the geometry of the bevel and acts as a reflector, simulating a defect of a known shape and size. The block also includes notches 14cn1, 14cn2, 14cn3, 14rn1, 14rn2, 14rn3 in the cap and root regions, simulating defects near the inner and outer pipe diameters. The various reference numerals used in FIG. 5 are summarised as follows:

| | |
|---|---|
| Cap Notches 1 to 3 | 14cn1, 14cn2, 14cn2 |
| Cap | 14c |
| Fill layers 1 to 7 | 14f1 to 14f7 |
| Hot Pass | 14h |
| Root | 14r |
| Root Notches 1 to 3 | 14rn1, 14rn2, 14rn3 |

The calibration block is used to generate a look-up table for use when performing NDT inspections on a pipe having a bevel geometry and material composition corresponding to that of the calibration block. For each measurement made during the NDT method, a reflector is provided in the calibration block to simulate a defect. The reflector is sized to correspond to the maximum size of defect able to be measured by the particular scan concerned (typically the full height of the zone being inspected). The calibration table is produced by assuming the measured reflection to be at greatest possible amplitude (i.e. 100% amplitude) for the reflector The look-up table may then be used to correlate the amplitude of reflected radiation with defect size on a zone-by-zone basis. For example, if a reflection is detected when directing radiation at the Fill 3 zone at 80% of the full refection amplitude, then the defect can be assumed to have a size of 1.9 mm. In order for the look-up table to provide accurate defect measurements, the NDT measurements performed, the pipe material, pipe diameter and wall thickness and bevel geometry must all match as closely as possible those that will be used in the field. In the third embodiment, there is also some accounting for overlapping measurements. Thus, a defect in or extending to a zone adjacent to that being scanned may affect the amplitude measurements made, as a result of the difficulty of precisely focussing beams of ultrasonic radiation solely be means of focal laws. Such overlap (or "overtrace") may be accounted for by means of measurements made on the calibration block. Thus, each reflector for each zone may be spatially separated from adjacent zones in the block (by means of being spaced apart around the circumference of the block) and measurements made not only of the reflection by the reflector of radiation directed directly at the zone in which the reflector is located but also of the reflection by the reflector of radiation directed at adjacent zones. Overtrace correction may then be applied to any measurements made in the field where reflections of radiation are observed from adjacent zones.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

The weld to be inspected may be divided into zones other than those described above. For example, there may be more or fewer than five fill zones, and the weld to be inspected may have no LOP zones. The shape of the bevel may be different to that shown. Gas tungsten inert welding (GTAW) torches may be used to perform the welding. The above method can be performed on pipes, other than underwater gas/oil conveying pipelines that lay on the seabed. The illustrated embodiments are of particular use in fatigue sensitive welds for example as are provided on steel catenary risers. The principles of the embodiments can also be applied to NDT inspection of onshore girth welds, for example during the onshore prefabrication of double-joint austenitic girth welds. The weld does necessarily need to be an austenitic weld in order for the invention to be beneficial or advantageous.

In certain modes of operation, radiation emitted by a phased array on one side of the weld may be detected by a phased array on the opposite side of the weld.

In the embodiment described with reference to FIG. 3, the beams emitted by one set of transducers includes a second surface wave beam of ultrasonic radiation incident on the weld as a compression (longitudinal) wave.

Alternatively, the second beam may be in the form of one of a plurality of the unfocussed longitudinal wave beams described above in relation to the volumetric scanning of the weld.

Several scans of the weld may be performed in parallel. For example, as long as two elements are not required to perform the same scan at the same time, respective sets of elements may be operated in parallel. Other scans may be performed quickly one after the other, where some of the elements in the two successive scans are the same.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A method for the non-destructive inspection of an austenitic weld between a first metal pipe and a second metal pipe sections during a method of laying a pipeline, wherein the method comprises the following steps:
providing a plurality of ultrasonic transducers, able to transmit and detect ultrasonic radiation, comprising two or more ultrasonic transducers arranged as a phased array,
emitting from the phased array a first beam of ultrasonic radiation, focussed to be incident on a first region of the weld,
emitting from one or more of the plurality of ultrasonic transducers a second beam of ultrasonic radiation incident on a second region of the weld,
emitting from the phased array a third beam of ultrasonic radiation, focussed to be incident on a third region of the weld as a transverse wave, the third region covering the first region,
at least two of the first, second and third beams being emitted substantially contemporaneously,
the first beam comprising a transverse wave which is reflected on an inner wall of one of the pipes, a mode converted longitudinal wave resulting from such a reflection
detecting with one or more of the plurality of ultrasonic transducers radiation from the first, second and third regions resulting from the incidence of the first, second and third beams, said detecting including detecting an amplitude of radiation received as a result of reflection, from a defect in the weld, of said mode-converted longitudinal wave,
extracting information from the detected radiation, said information including a measure of the amplitude of the radiation received as a result of reflection from the defect of said mode-converted longitudinal wave,
using such information to detect a presence of the defect,
using said measure of the amplitude of the reflected radiation to provide a measure of the size of the defect, and
using the third beam to confirm that the defect is present at the first region.

2. A method according to claim 1, wherein the step of emitting the first beam from the phased array is conducted such that the beam is incident on the first region of the weld as a longitudinal wave.

3. A method according to claim 2, wherein the longitudinal wave incident on the first region is the mode-converted longitudinal wave resulting from reflection of the transverse wave on the inner wall of one of the pipes.

4. A method according to claim 1, wherein the step of emitting the third beam from the phased array is conducted such that the beam is incident on the third region of the weld as a transverse wave.

5. A method according to claim 1, wherein said measure of the size of the defect resulting from said measure of the amplitude of the reflected radiation is provided by correlating the amplitude thus detected with the size of the defect by means of a look-up table.

6. A method according to claim 5, wherein the look-up table correlates the amplitude of reflected radiation with defect size on a zone-by-zone basis, there being at least six different zones including at least four fill zones, at least one root zone, and at least one cap zone, the beam of radiation from which the reflection is measured is focussed to be incident on only one zone.

7. A method according to claim 1, wherein all of the first, second and third beams are emitted substantially contemporaneously.

8. A method according to claim 7, wherein the second region is different from the first region.

9. A method according to claim 1, wherein the method includes a step of emitting from one or more of the plurality of ultrasonic transducers a beam of ultrasonic radiation incident on the second region of the weld in the form of a longitudinal wave.

10. A method according to claim 1, wherein the method includes a step of emitting from one or more of the plurality of ultrasonic transducers a beam of ultrasonic radiation incident on a region of the weld in the form of a surface wave along an exterior surface of one of the pipe-sections.

11. A method according to claim 1, wherein the method is performed such that:
ultrasonic radiation is emitted from the phased array to a first zone of the weld and to a second zone of the weld, and radiation transmitted from the first and second zones resulting from the incidence of the emitted radiation on the first and second zones is detected with the phased array, the radiation and the phased array being such that it is possible to distinguish between radiation from the first zone from radiation from the second zone.

12. A method according to claim 1, wherein the method includes steps of emitting from one or more of the plurality of ultrasonic transducers a beam of ultrasonic radiation incident on a part of the root of the weld, and detecting with one or more of the plurality of ultrasonic transducers radiation from the root of the weld resulting from the incidence of the beam directed at the root, wherein the step of using the information extracted from the detected radiation includes providing two different visual representations of the information extracted.

13. A method according to claim 12, wherein the two visual representations include an A-scan representation and a B-scan representation.

14. A method according to claim 1, wherein the method includes emitting and detecting ultrasonic radiation with two or more of the transducers of the plurality of ultrasonic transducers operating in a pitch-catch mode substantially contemporaneously with detecting ultrasonic radiation with one or more of the transducers of the plurality of ultrasonic transducers operating in a pulse-echo mode.

15. A method according to claim 1, further including providing measures of the location and size of the defect, the measures of the location and size of the defect being derived solely from ultrasound measurements.

16. A method according to claim 1, wherein the pipes are steel pipes, clad with a corrosion resistant alloy.

17. A non-destructive inspection apparatus comprising a control system and a plurality of ultrasonic transducers, wherein the control system is configured to control the plurality of ultrasonic transducers to operate in accordance with the method of claim 1.

18. A method according to claim 1, wherein the measure of the size of the defect provided by using said measure of the amplitude of the reflected radiation is within the range of 0.1 mm to 3.0 mm.

19. A non-destructive inspection apparatus comprising a control system and a plurality of ultrasonic transducers, wherein the control system is configured to control the plurality of ultrasonic transducers to operate in accordance with the method of claim 1 and the apparatus is configured to be capable of detecting a flaw having a maximum dimension of 0.3 mm.

20. A method for the non-destructive inspection of an austenitic weld between a first metal pipe and a second metal pipe sections during a method of laying a pipeline, wherein the method comprises the following steps:

providing a plurality of ultrasonic transducers, able to transmit and detect ultrasonic radiation, comprising two or more ultrasonic transducers arranged as a phased array, emitting from the phased array a first beam of ultrasonic radiation, focussed to be incident on a first region of the weld, emitting from one or more of the plurality of ultrasonic transducers a second beam of ultrasonic radiation incident on a second region of the weld, emitting from the phased array system a third beam of ultrasonic radiation, focussed to be incident on a third region of the weld, at least two of the first, second and third beams being emitted substantially contemporaneously, detecting with one or more of the plurality of ultrasonic transducers radiation from the first, second and third regions resulting from the incidence of the first, second and third beams, extracting information from the detected radiation, and using such information to provide an indication from which the likelihood of a defect in the weld may be discerned, wherein at least one of the first, second and third beams comprises a transverse wave which is reflected on an inner wall of one of the pipes, and said at least one of the first, second and third beams comprises a mode converted longitudinal wave resulting from the reflection of the transverse wave on the inner wall, wherein the method further includes the steps of detecting the amplitude of the radiation received as a result of the reflection of one of the first to third beams from a defect, and correlating the amplitude thus detected with a size of the defect by means of a look-up table, wherein the look-up table correlates the amplitude of reflected radiation with defect size on a zone-by-zone basis, there being at least six different zones including at least four fill zones, at least one root zone, and at least one cap zone, the beam of radiation from which the reflection is measured is focussed to be incident on only one zone, and wherein the method includes an initial step of creating the look-up table in respect of the particular geometry of the weld, the weld being formed within a weld bevel having a particular bevel geometry, by performing the following step in respect of each zone:

measuring the amplitude of reflected radiation from an acoustic reflector having a known size located in a calibration test-piece, the test-piece and acoustic reflector having a geometry corresponding to the bevel geometry so as to give representative amplitude measurements for use in the look-up table.

\* \* \* \* \*